United States Patent

Whiteley et al.

[11] Patent Number: 5,962,223
[45] Date of Patent: *Oct. 5, 1999

[54] DETECTION OF SPECIFIC SEQUENCES IN NUCLEIC ACIDS

[75] Inventors: Norman M. Whiteley; Michael W. Hunkapiller, both of San Carlos; Alexander N. Glazer, Orinda, all of Calif.

[73] Assignee: The Perkin-Elmer Corporation, Foster City, Calif.

[*] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 08/574,826

[22] Filed: Dec. 19, 1995

Related U.S. Application Data

[63] Continuation of application No. 08/257,219, Jun. 8, 1994, Pat. No. 5,521,065, which is a continuation of application No. 07/895,707, Jun. 9, 1992, abandoned, which is a continuation of application No. 07/361,407, Jun. 5, 1989, Pat. No. 5,242,794, which is a continuation of application No. 06/681,055, Dec. 13, 1984, Pat. No. 4,883,750.

[51] Int. Cl.⁶ .............................. C12Q 1/68; C07H 21/04; C12P 19/34
[52] U.S. Cl. .................... 435/6; 435/5; 435/91.5; 435/91.52; 435/810; 536/24.3; 536/24.31; 536/24.32; 536/24.33
[58] Field of Search .................. 435/6, 5, 810, 435/25.4, 91.5, 91.52; 536/24.3, 24.31, 24.33, 24.32; 935/6, 8, 78

[56] References Cited

U.S. PATENT DOCUMENTS

| | | | |
|---|---|---|---|
| 4,358,535 | 11/1982 | Falkow et al. | 435/5 |
| 4,395,486 | 7/1983 | Wilson et al. | 435/6 |
| 4,486,539 | 12/1984 | Ranki et al. | 436/504 |
| 4,710,465 | 12/1987 | Weissman et al. | 435/91 |
| 4,775,619 | 10/1988 | Urdea | 435/6 |
| 4,820,630 | 4/1989 | Taub | 435/5 |
| 5,288,609 | 2/1994 | Engelhardt | 435/6 |

FOREIGN PATENT DOCUMENTS

| | | |
|---|---|---|
| 70685 A2 | 1/1983 | European Pat. Off. |
| 154505 A2 | 9/1985 | European Pat. Off. |

OTHER PUBLICATIONS

Langer et al, Proceedings National Academy of Sciences, USA (Nov. 1981) 78(11) 6633–6637.

(List continued on next page.)

*Primary Examiner*—Carla J. Myers
*Attorney, Agent, or Firm*—Vincent M. Powers; Dehlinger & Associates

[57] ABSTRACT

The invention provides a method for diagnosis of genetic abnormalities or other genetic conditions which can be readily automated. The method is used to determine the presence or absence of a target sequence in a sample of denatured nucleic acid and entails hybridizing the sample with a probe complementary to a diagnostic portion of the target sequence (the diagnostic probe), and with a probe complementary to a nucleotide sequence contiguous with the diagnostic portion (the contiguous probe), under conditions wherein the diagnostic probe remains bound substantially only to the sample nucleic acid containing the target sequence. The diagnostic probe and contiguous probe are then covalently attached to yield a target probe which is complementary to the target sequence, and the probes which are not attached are removed. In the preferred mode, one of the probes is labeled so that the presence or absence of the target sequence can then be tested by melting the sample nucleic acid-target probe duplex, eluting the dissociated target probe, and testing for the label. In another embodiment, the testing is accomplished without first removing probes not covalently attached, by attaching a hook to the probe that is not labeled, so that the labeled target probe may be recovered by catching the hook. In both instances, the presence of both the diagnostic probe and the contiguous probe is required for the label to appear in the assay. The above method is then applied to the detection of genetic diseases.

20 Claims, 4 Drawing Sheets

OTHER PUBLICATIONS

Barker, D.G. et al., "An improved assay for DNA ligase reveals temperature–sensitive activity in cdc9 mutants of *Saccharomyces cerevisiae*" *Mol. Gen. Genet* 200:458 (1985).

Besmer, P., et al., "Studies on Polynucleotides" *J.Mol. Biol.* 72:503 (1972).

Conner, B.J., et al., "Detection of sickle cell β–globin allele by hybridization with synthetic oligonucleotides," *PNAS USA 80*:278–282 (1983).

Harvey, C.L. et al., "Enzymatic Breakage and Joining of Deoxyribonucleic Acid" *The Journal of Biological Chemistry 246*(14):4523 (1971).

Harvey, C.L., & Wright, R., "Ligase Joining of Oligodeoxythymidylates" *Biochemistry 11*(14):2667 (1972).

Higgins, P.N., & Cozzarelli, N.R., "DNA–Joining Enzymes: A Review" *Methods in Enzymology 68*:50 (1979).

Kidd, V.J., et al., "Prenatal Diagnosis of a $\alpha_1$–Antitrypsin Deficiency by Direct Analysis of the Mutation Site in the Gene" *Medical Intelligence 310*(10):639 (1984).

Kennell, D.E., "Principles and Practices of Nucleic Acid Hybridization" in Progress in Nucleic Acid Research and Molecular Biology (Davidson, J.N. et al. editors) Academic Press, N.Y., 1971, pp. 259–301.

Klausner, A., & Wilson, T., "Gene Detection Technology Opens Doors for Many Industries" *Biotechnology,* Aug. 1983, pp. 471–478.

Lehman, I.R., "DNA Ligase: Structure, Mechanism, and Function" *Science 186*:790 (1974).

Meinkoth, J., & Wahl, G., "Hybridization of Nucleic Acids Immobilized on Solid Supports" *Analytical Biochemistry,* 138:267 (1984).

Olivera, B.M., et al., "On the Mechanism of the Polynucleotide Joining Reaction" *Cold Spring Harbor Symposium on Quantitative Biology* p. 27 (1968).

Olivera, B.M., et al., "Enzymic Joining of Polynucleotides" *J. Mol. Biol.,* 36:261 (1968).

Schwarz, E., et al., "Nucleotide sequence of cro, cII and part of the O gene in phage λ DNA" *Nature 272*:410 (1978).

Sgaramella, V., & Ehrlich, D., "Use of the T4 Polynucleotide Ligase in The Joining of Flush–Ended DNA Segments Generated by Restriction Endonucleases" *Eur. J. Biochem.* 86:531 (1978).

Singer–Sam, J., et al., "Isolation of a cDNA clone for human X–linked 3–phosphoglycerate kinase by use of a mixture of synthetic oligodeoxyribonucleotides as a detection probe" *Proc. Natl. Acad. Sci. USA 80*:802 (1983).

Southerm E.M., "Detection of Specific Sequences Among DNA Fragments Separated by Gel Electrophoresis" *J. Mol. Biol.* 98:503 (1975).

Tsiapalis, C.M., & Narang, S.A., "On the Fidelity of Phage $T_4$–Induced Polynucleotide Ligase in the Joining of Chemically Synthesized Deoxyribooligonucleotides." *Biochemical and Biophysical Research Communications 39*(4):631 (1970).

Weiss, B., & Richardson, C.C., "Enzymatic Breakage and Joining of Deoxyribonucleic Acid. I. Repair of Single–Strand Breaks In DNA by an Enzyme System from *Escherichia Coli* Infected with $T_4$ Bacteriophage" *Proc. Natl. Acad. Sci.* 57:1201 (1967).

M and Z Oligonucleotide Analysis of Family

DETECTION OF SPECIFIC SEQUENCES IN NUCLEIC ACIDS

This is a continuation of application Ser. No. 08/257,219, filed Jun. 8, 1994, now U.S. Pat. No. 5,521,065 which is a file-wrapper-continuation of application Ser. No. 07/895,707 filed Jun. 9, 1992, abandoned, which is a continuation of application Ser. No. 07/361,407 filed Jun. 5, 1989, U.S. Pat. No. 5,242,794, which is a continuation of application Ser. No. 06/681,055 filed Dec. 13, 1984, U.S. Pat. No. 4,883,750.

BACKGROUND OF THE INVENTION

This invention relates to the detection of specific sequences of nucleotides in a variety of nucleic acid samples, and more particularly to those which contain a sequence characterized by a difference in a single base pair from a standard sequence.

In recent years it has been found that many human diseases can be traced directly to genetic mutations. Some commonly known examples include cystic fibrosis, muscular dystrophy, Tay-Sachs disease, hemophilias, phenylketonuria and sickle-cell anemia. Of the over 500 recognized genetic diseases, many can be traced to single base pair mutations.

Two important techniques have been developed in the art for directly detecting these single base pair mutations. However, neither of these approaches can be easily automated. An automated technique is desirable since it has the potential to decrease labor time, decrease the level of skill required, and should increase reliability. In the first of these prior art techniques, the presence or absence of the mutation in a subject is detected by analysis of a restriction digest of the subject's DNA using Southern blotting. (E. Southern, "Detection of Specific Sequences Among DNA Fragments Separated by Gel Electrophoresis," *Journal of Molecular Biology*, 98, (1975), 503). For example, sickle-cell disease results from a mutation that changes a glutamic acid residue, coded by the triplet GAG, for a valine residue, coded by GTG, at position 6 in the β-globin chain of hemoglobin. In the mutation of A to T in the base sequence of the β-globin gene, a restriction site for the enzyme MstII (as well as sites for other restriction enzymes) is eliminated. The sickle hemoglobin mutation can therefore be detected by digesting sickle-cell and normal DNA with MstII and using Southern blotting to distinguish the restriction fragments. Normal DNA will generate an MstII fragment 1.1 kilobases long whereas sickle-cell DNA will generate a fragment 1.3 kilobases long.

The specifics of the Southern blot technique are as follows. First, the sample DNA is cut with a restriction enzyme (in this case MstII), and the resultant fragments are separated, based on their size, typically by agarose gel electrophoresis. The gel is then laid onto a piece of nitrocellulose, and a flow of an appropriate buffer is set up through the gel, perpendicular to the direction of electrophoresis, toward the nitrocellulose filter. The flow causes the DNA fragments to be carried out of the gel onto the filter, where they bind, so that the distribution of the DNA fragments in the gel is replicated on the nitrocellulose. The DNA is then denatured and fixed onto the filter. A radioactively labeled probe, complementary to the sequence under study, is then hybridized to the filter, the probe hybridizing to the specific fragment containing the sequence under study. Autoradiography of the nitrocellulose filter then identifies which fragment or fragments contain the sequence under study, each fragment being identified according to its molecular weight. A variation on this technique is to hybridize and do autoradiography directly in the gel, rather than on a nitrocellulose filter. Also, other restriction enzymes may be used provided one of the resulting fragments contains the mutation site of interest.

This direct Southern blot approach used for sickle-cell disease cannot be used, however, for genetic diseases where the mutation does not alter a restriction site, for example, as in $\alpha_1$-antitrypsin deficiency, a genetic disease which subjects the individual to greatly increased risk of developing pulmonary emphysema or infantile liver cirrhosis. There, the mutant gene has a single base change (G→A) that leads to an amino acid substitution (GLU→LYS) at residue 342, thereby producing a non-functional protein. This substitution does not, however, create or destroy a restriction site for any of the currently known restriction enzymes as in sickle-cell anemia. Hence, a straightforward analysis of restriction fragments to search for an altered restriction site is not possible. A technique has been developed, however, which can be used in this situation. (See "Detection of Sickle-cell $\beta^s$-globin Allele by Hybridization with Synthetic oligonucleotides," by Brenda J. Conner, et al., Proc. Natl. Acad. Sci., Vol 80, pp. 278–282, (January 1983), and "Prenatal Diagnosis of $\alpha_1$-Antitrypsin Deficiency by Direct Analysis of the Mutation Site in the Gene," by Vincent J. Kidd, et al., New England Journal of Medicine, Vol. 310, No. 10, (March 1984).) This second technique is to synthesize a 19-base long oligonucleotide (hereinafter a 19-mer) that is complementary to the normal $\alpha_1$-antitrypsin sequence around the mutation site. The 19-mer is labeled and used as a probe to distinguish normal from mutant genes by raising the stringency of hybridization to a level at which the 19-mer will hybridize stably to the normal gene, to which it is perfectly complementary, but not to the mutant gene, with which it has the single base pair mismatch. (By stringency, it is meant the combination of conditions to which nucleic acids are subject that cause the duplex to dissociate, such as temperature, ionic strength, and concentration of additives, such as formamide. Conditions that are more likely to cause the duplex to dissociate are called "higher" stringency, e.g., higher temperature, lower ionic strength, and higher concentration of formamide.) Similarly, if it is desired to detect the mutant gene, instead of the normal gene, a 19-mer is used which is complementary to the mutant $\alpha_1$-antitrypsin sequence around the mutant site. Hence, by using synthetic probes complementary to the sequence of interest in a Southern blot analysis, and varying the stringency, normal and mutant genes can be distinguished.

Although this latter technique is straightforward, it is not without difficulties, especially if an automated procedure is desired. Generally, both the matched and mismatched probes undergo hybridization to the fragment excised by the restriction enzyme, the matched probe being bound at all 19 bases, and the mismatched probe at at most 18 bases. Hence, the relative difference in binding energy between the two probes is quite small. Thus changes in stringency must be delicate enough to dissociate the mismatched probe without also dissociating the matched probe. This would not be a problem with respect to automating the technique were it not for the considerable retention of 19-mer probes by high-molecular weight DNA, presumably due to DNA sequences in the human genome that are somewhat homologous with the synthetic DNA probes used, although this cannot be stated with certainty. This large excess of somewhat homologous sequences in comparison with the $\alpha_1$-antitrypsin gene obscures the experimental results and must be treated as background noise in any automated technique and is presently resolved by subjecting the sample to gel electrophoresis and Southern blotting. (See FIGS. 1A and 1B showing the Southern blots for the $\alpha_1$-antitrypsin detection scheme reported by Kidd, et al., above.) In this particular instance, this background did not interfere with the diagnosis since a previously developed restriction map indicated that only the band at 2.4 kilobases was relevant. However, it can be seen that most of the probe actually bound is not in the 2.4 kilobase band. In this instance, the time and labor consuming restriction digest and electrophoresis were carried out to separate the DNA sequence of interest, the 2.4 kilobase fragment, from the bulk of the DNA, thereby essentially eliminating background problems.

In most situations involving genetic disease, such restriction maps will already be available, so that the above technique can be quite generally applicable. However, such a technique is not easily automated, just as the previous technique used for sickle-cell disease is not easily automated. What is needed is a technique for detecting single base pair differences between sequences of nucleotides which does not require the use of restriction enzymes, gel electrophoresis, or time consuming autoradiography, and which is readily amenable to automation.

SUMMARY OF THE INVENTION

The invention provides a method for diagnosis of genetic abnormalities or other genetic conditions which can be readily automated. The method takes advantage of the low probability that a particular diagnostic sequence which may be found in a number of irrelevant locations in the genome, will be extended by the same or similar contiguous sequence at these irrelevant locations. By requiring that both the diagnostic and contiguous sequence be present, background noise caused by spurious binding of the diagnostic sequence is eliminated, and the necessity for separating the relevant sequence from the background using such techniques as electrophoresis or chromatography is eliminated.

In one aspect, the invention relates to a method for determining the presence or absence of a target sequence in a sample of denatured nucleic acid which entails hybridizing the sample with a probe complementary to a diagnostic portion of the target sequence (the diagnostic probe), and with a probe complementary to a nucleotide sequence contiguous with the diagnostic portion (the contiguous probe), under conditions wherein the diagnostic probe remains bound substantially only to the sample nucleic acid containing the target sequence. The diagnostic probe and contiguous probe are then covalently attached to yield a target probe which is complementary to the target sequence, and the probes which are not attached are removed. In the preferred mode, one of the probes is labeled so that the presence or absence of the target sequence can then be tested by melting the sample nucleic acid-target probe duplex eluting the dissociated target probe, and testing for the label.

In another approach, the testing is accomplished without first removing probes not covalently attached, by attaching a hook to the probe that is not labeled, so that the labeled target probe may be recovered by catching the hook.

In both instances, the presence of both the diagnostic probe and the contiguous probe is required for the label to appear in the assay. This eliminates the background which had previously been segregated by the size separations accomplished by the Southern blot technique. Hence, the predominant detriments of the prior art techniques have been eliminated, i.e., no treatment with restriction enzymes is required, no gel electrophoresis is required, and no autoradiography is required.

The above method is directly applicable to detecting genetic diseases, particularly those resulting from single base pair mutations, and may be made more precise by comparative results from tests wherein each of the normal and abnormal sequence is made the target sequence. For example, in this embodiment, two diagnostic probes are synthesized, one for the normal gene and one for the mutated gene, and the above method is carried out for each probe independently. The DNA from individuals homozygous for the normal gene will show a high count of label for the probe specific to the normal gene and a low count for the gene specific for the mutated gene. Similarly, DNA from individuals homozygous for the mutated gene, will show a high count for the probe specific to the mutated gene and a low count for the normal probe. Heterozygous individuals will show a count for both the normal probe and mutated probe which are equal and intermediate between the high and low counts for homozygous and heterozygous individuals. Use of only one diagnostic probe, preferably specific to the mutated sequence of interest, is also possible. Using the general method described earlier, the detection scheme is first calibrated so that the amount of label expected corresponding to homozygous normal, homozygous mutant, and heterozygous individuals is known. Then the method is carried out on the sample DNA, and the amount of label detected is compared with the calibration.

DETAILED DESCRIPTION OF THE INVENTION

Figure 1A:
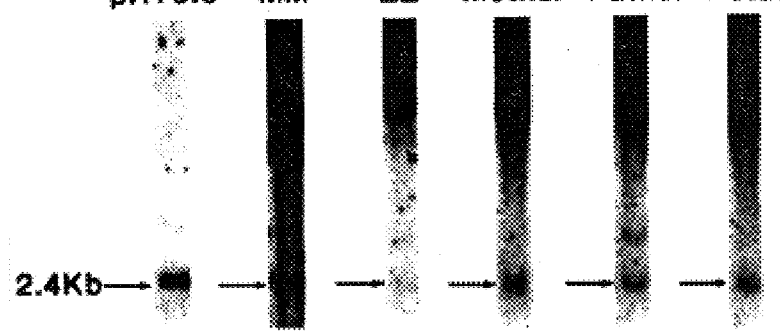
FIG. 1A shows the results of a test for $\alpha_1$-antitrypsin deficiency. The test used a Southern blot for DNA samples from cloned $\alpha_1$-antitrypsin gene (pAT9.6), the MM (normal-normal) and ZZ (deficient-deficient) homozygote cellular DNA controls, the parents, and the fetus at risk, hybridized to a normal M oligomer probe. The band at 2.4 kb indicates the presence of the normal gene.
Figure 1B:
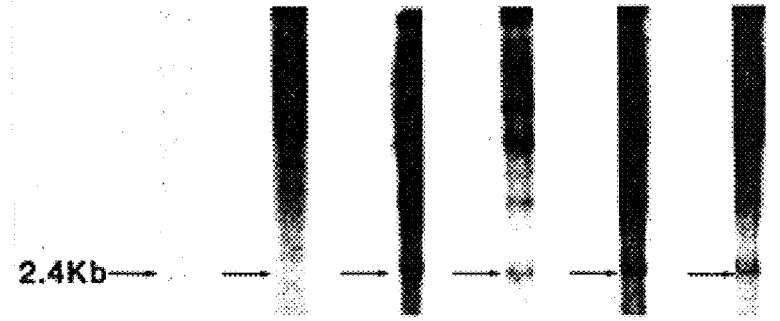
FIG. 1B shows the same DNA samples hybridized to a deficient Z oligomer probe. The band at 2.4 kb indicates the presence of the deficient gene.

For the purposes of the subsequent description, the following definitions will be used:

"Target sequence" is a nucleic acid sequence, the presence or absence of which is desired to be detected. In the context of a preferred application of the method of the invention, it is a sequence which forms part of a coding region in a gene associated with a genetic disease, such as sickle-cell anemia. In many such diseases, the presence of the genetic aberration is characterized by small changes in the coding sequence; most frequently, normal individuals have sequences which differ by only one nucleotide from the corresponding sequences present in individuals with the genetic "deficiency." In the method of the invention, either the normal or altered sequence can be used as the target sequence.

"Diagnostic portion" refers to that portion of the target sequence which contains the nucleotide modification, the presence or absence of which is to be detected.

"Contiguous portion" refers to a sequence of DNA which is a continuation of the nucleotide sequence of that portion of the sequence chosen as diagnostic. The continuation can be in either direction.

It will be recognized, based on the disclosure below, that the precise position of the selected diagnostic portion is arbitrary, except that it must contain the nucleotide(s) which differentiate the presence or absence of the target sequence. Thus, the contiguous portion continues the sequence of this arbitrarily chosen diagnostic portion.

"Hybridization" and "binding" in the context of probes and denatured DNA are used interchangeably. Probes which are hybridized or bound to denatured DNA are aggregated to complementary sequences in the polynucleotide. Whether or not a particular probe remains aggregated with the polynucleotide depends on the degree of complementarity, the length of the probe, and the stringency of the binding conditions. The higher the stringency, the higher must be the degree of complementarity, and/or the longer the probe.

"Covalently attaching" refers to forming a covalent chemical bond between two substances.

"Ligating" refers to covalently attaching two polynucleotide sequences to form a single sequence. This is typically performed by treating with a ligase which catalyzes the formation of a phosphodiester bond between the 5' end of one sequence and the 3' end of the other. However, in the context of the invention, the term "ligating" is intended to also encompass other methods of covalently attaching such sequences, e.g., by chemical means, and the terms "covalently attaching" and "ligating" will be used interchangeably.

"Probe" refers to an oligonucleotide designed to be sufficiently complementary to a sequence in a denatured nucleic acid to be probed, in relation to its length, to be bound under selected stringency conditions.

"Diagnostic probe" refers to a probe which is complementary to the diagnostic portion.

"Contiguous probe" refers to a probe which is complementary to the contiguous portion.

"Target probe" refers to a probe which is complementary to the target sequence and which is made by covalently attaching (ligating) the diagnostic probe and the contiguous probe.

"Hook" refers to a modification of a probe that enables the experimenter to rapidly and conveniently isolate probes containing this modification by "catching" the hook. The interaction between hook and catching mechanism can be, for example, covalent bonding or ligand receptor binding of sufficient tightness. Such hooks might include antigens which can be recovered by antibody, specific DNA sequences which can be recovered by complementary nucleic acids, and specific reactive chemical groups which can be recovered by appropriate reactive groups.

"Label" refers to a modification to the probe nucleic acid that enables the experimenter to identify the labeled nucleic acid in the presence of unlabeled nucleic acid. Most commonly, this is the replacement of one or more atoms with radioactive isotopes. However, other labels include covalently attached chromophores, fluorescent moeities, enzymes, antigens, groups with specific reactivity, chemiluminescent moeities, and electrochemically detectable moeities, etc.

In a preferred embodiment of the method, certain preliminary procedures are necessary to prepare the sample nucleic acid and the probes before the assay may be performed.

Sample Preparation

The sample nucleic acid is denatured and usually immobilized, typically by being bound to a solid support such as nitrocellulose filter paper. Techniques for denaturing and binding are well known in the art. (See for example, P. 331, Molecular Cloning, by Maniatis, Fritsch, and Sambrook, Cold Spring Harbor Laboratory, 1982, reproduced as Appendix A herein.)

The non-specific binding sites available in the system are then blocked. In the typical case using nitrocellulose filter paper as the solid support, the nucleic acid-paper is treated so that additional nucleic acid will not become irreversibly bound to the paper. This is accomplished, for example, by incubating the nucleic acid and filter for two hours at 80° C. in 40× Denhardt's solution (40× Denhardt's solution is 8 g/l bovine serum albumin, 8 g/l polyvinyl pyrolidone and 8 g/l Ficoll). Then the 40× Denhardt's is removed.

Probe Preparation

In those cases where the diagnostic probe and the contiguous probe are not already available, they must be synthesized. Apparatus for such synthesis is presently available commercially, such as the Applied Biosystems 380A DNA synthesizer and techniques for synthesis of various nucleic acids are available in the literature.

In one embodiment, the probes are prepared for ligation, e.g., if ligase is to be used, the probe which will have its 5' end adjacent the 3' end of the other probe when hybridized to the sample nucleic acid is phosphorylated in order to later be able to form a phosphodiester bond between the two probes. One of the probes is then labeled. This labeling can be done as part of the phosphorylation process above using radioactive phosphorus, or can be accomplished as a separate operation by covalently attaching chromophores, fluorescent moieties, enzymes, antigens, chemiluminescent moieties, groups with specific binding activity, or electrochemically detectable moieties, etc. (Appendix B provides a detailed description for 5' end labeling with $^{32}P$ using $T_4$ polynucleotide kinase.)

As another aspect of the invention, the diagnostic and contiguous probes useful for the invention may be packaged as a test kit. A diagnostic probe and a contiguous probe for detecting a particular target sequence associated with a genetic disease are synthesized and one labelled. One of the probes is also terminated in a manner that permits ligation to the other probe. The two probes can then be packaged with appropriate instructions so that the method may be practiced.

Method of the Invention

Step 1.

Hybridize the probe which will remain bound under the more stringent conditions. (Generally, either probe may be longer, and thus remain bound under more stringent conditions. However, for some sequences of nucleotides, the shorter probe may be the one more strongly bound.) The sample nucleic acid is incubated with this probe under conditions that promote specific binding of the probe to only the complementary sequences in the sample nucleic acid.

Step 2.

Hybridize the probe which will remain bound under the less stringent conditions. Again, the sample nucleic acid is incubated, this time with the other probe under conditions which will promote specific binding to only complementary sequences in the sample nucleic acid. Since probe from Step 1 will remain bound under the less stringent conditions required for this probe, hybridization of this probe to the sample nucleic acid will not materially affect the earlier hybridization.

Substep 1a or 2a.

Remove a substantial portion of the diagnostic probe which is not perfectly bound. (If the probe bound in Step 1 is the diagnostic probe, this is Step 1a and should be performed before Step 2, whereas, if the probe bound in Step 2 is the diagnostic probe, this is Step 2a and should follow Step 2.) This is accomplished by washing the sample nucleic acid at an appropriate stringency to dissociate from the nucleic acid any diagnostic probe which is not perfectly bound (i.e., not bound at all sites in the diagnostic portion) while leaving intact that which is perfectly bound. This procedure relies on the fact that there is an energy difference between probes which are perfectly bound and those which are not. In the situation under study, this difference may be quite small, since it can be the result of a single base pair mismatch in an entire diagnostic portion. Hence, the stringency needs to be carefully controlled during this removal process.

Step 3.

Ligate the two probes. The sample nucleic acid with the two probes bound thereto is treated with ligase or treated chemically to covalently attach the two probes, the 5' phosphate of one probe to the 3' hydroxyl of the other probe, at sites where they are hybridized to the nucleic acid adjacent to each other.

Step 4.

Increase the stringency to remove nearly all of the labeled probe that is not ligated to the other probe in Step 3 (>99%).

Following Step 4, for practical purposes, all that remains in the system is labeled target probe and any of several techniques can be used to detect it. For example, the label can be detected directly by autoradiography or counting, since the background from the non-specific binding of the labeled probe has been removed. In many situations, however, it is preferable and more easily quantitated to further increase the stringency to remove the target probe and to measure the amount of label coming off as the labeled target probe dissociates from the target sequence, a procedure which is easily automated.

In addition, this elution process provides more accurate results than detecting the bound target probe in situ, since it eliminates further background which can be contributed by irreversible binding of the labeled probe directly to the filter paper in those instances where the sample preparation has not been as effective as desired in blocking non-specific binding sites.

Figure 2A:
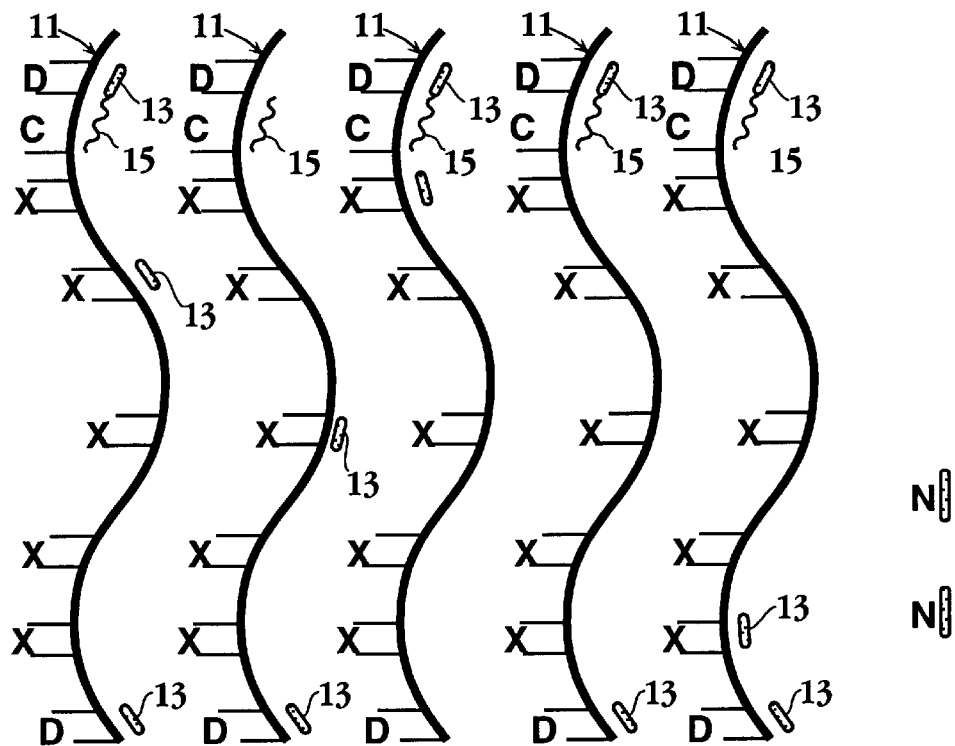
FIGS. 2A, 2B, and 2C illustrate various stages of the method of the invention.
Figure 2B:
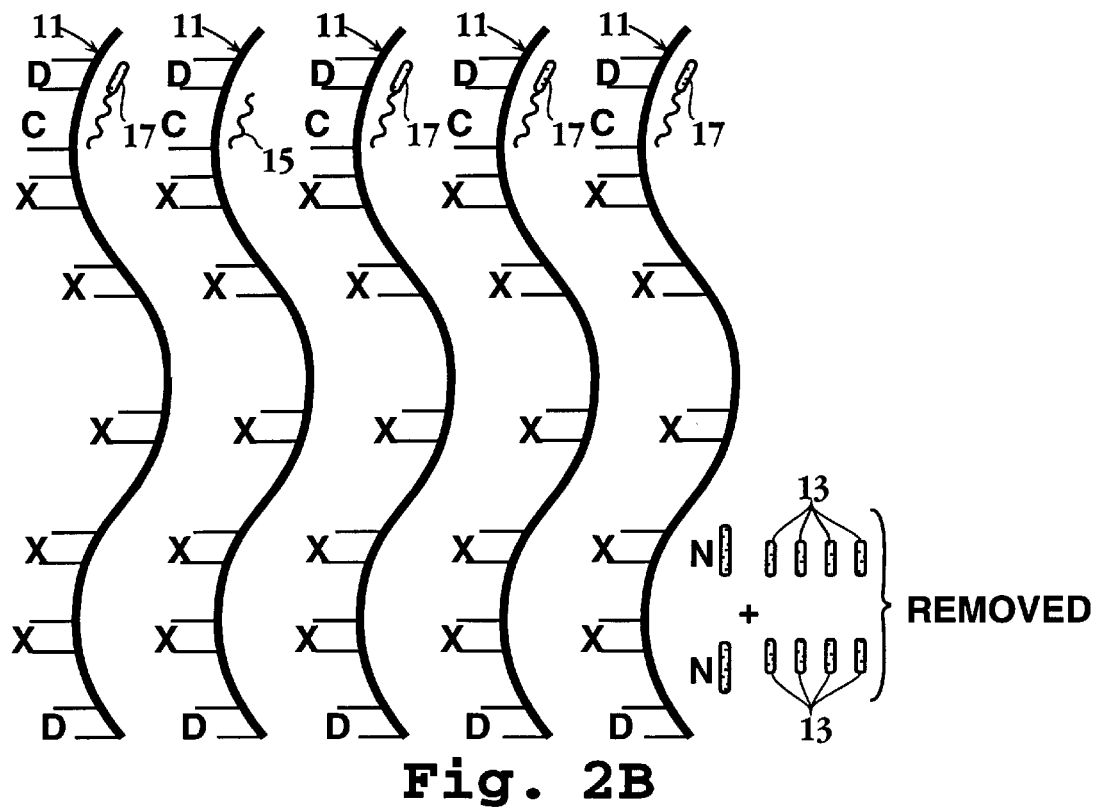
Figure 2C:
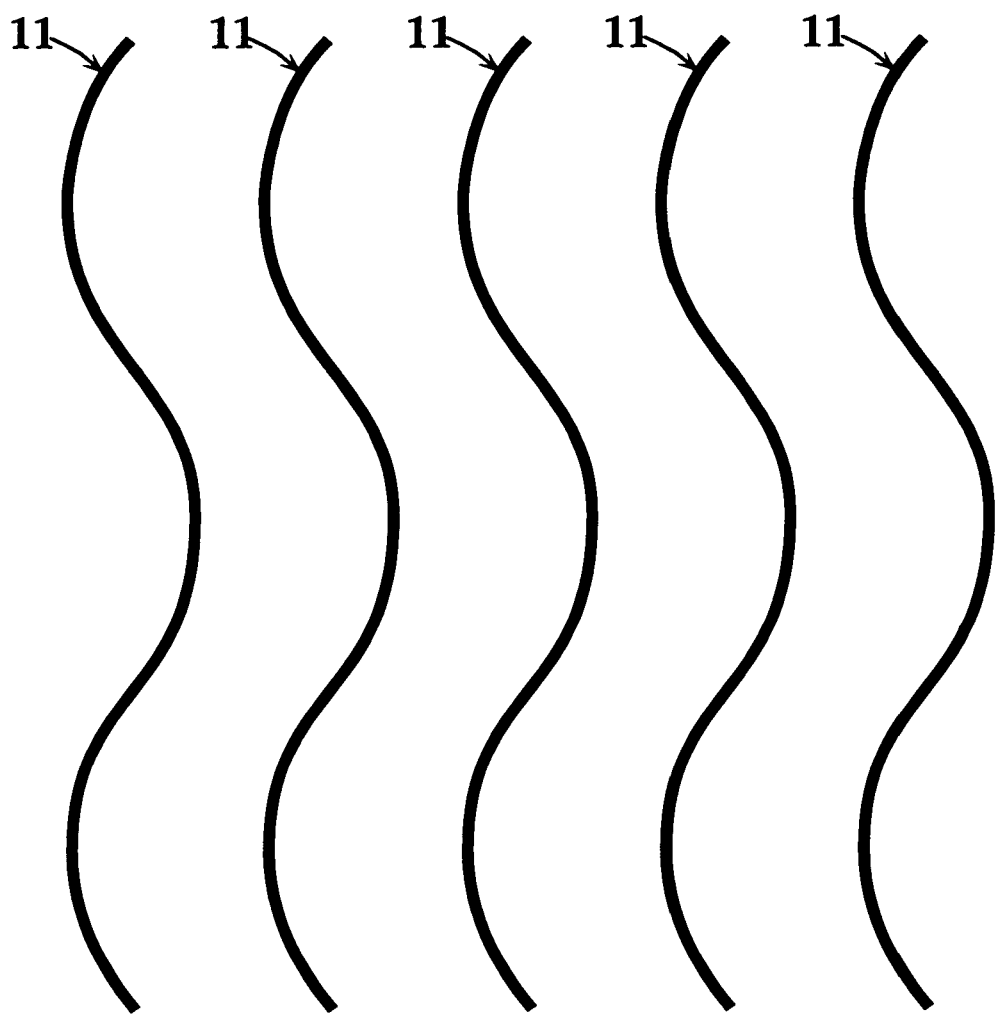
Figure 2C:
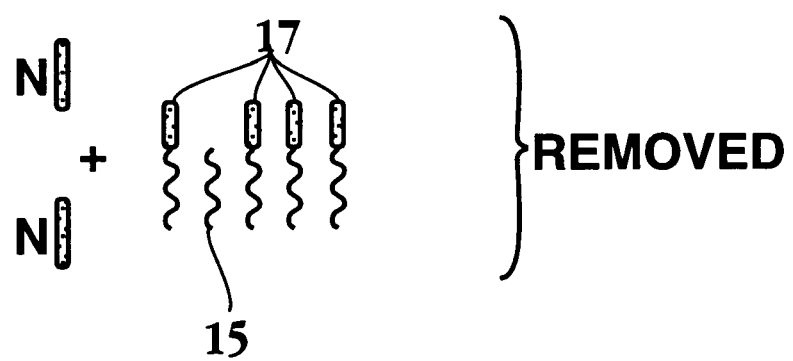

FIGS. 2A through 2C illustrate the principles of the above method at several stages, and particularly with regard to the detection of the diagnostic probe. It is assumed, for purposes of discussion, that the contiguous probe is the one which is more tightly bound, and that diagnostic probe is labeled.

FIG. 2A corresponds to the stage immediately after Steps 1 and 2, but before Step 2a, i.e., immediately following hybridization of a diagnostic probe 13 and a contiguous probe 15. In the Figure, the sample nucleic acid, represented by several denatured strands 11, has diagnostic portions D and a contiguous portion C. Where contiguous portion C and diagnostic portion D are adjacent designates the target sequence. Also included are portions X which correspond to any portion of the sample that is sufficiently similar in sequence to the diagnostic portions that the diagnostic probe will hybridize to that section. Areas N indicate any site in the system that will bind probes non-specifically. For purposes of illustration, it is assumed in FIG. 2A that 80% of the diagnostic sequences present will bind diagnostic probe and that 20% of the X sites bind probe and that all N sites bind probe. If the amount of diagnostic probe were measured at this stage to determine the number of target sequences present, there would be excessive background noise as occurred in the prior art due to the binding from all N sites, from D sites outside of the target sequence, and from a percentage of the X sites.

FIG. 2B illustrates the results of the method immediately after Step 4, where the diagnostic and contiguous probes have been ligated to form target probes 17 and the stringency has been increased to the point where all unligated diagnostic probes are no longer hybridized to the sample nucleic acid. If there are only few N sites present at this stage, the amount of the diagnostic probe can be measured in situ to determine the number of target sequences present.

FIG. 2C shows the stage after elution, i.e., where all the probes are removed, including target probes 17. Here, the amount of diagnostic probe which was originally hybridized to the target sequence can be determined without the background noise contributed by the binding to N sites, to X sites, and to D sites not in the target sequence.

The following example is provided as a specific application of the above technique and should not be construed to limit the scope of the invention. Bacteriophage λ-DNA was chosen as the sample nucleic acid in this example for two reasons. First, the expression of the λ genome is generally regarded as a model for genetically determined differentiation processes occurring in cells of higher organisms. Because of its model nature, λ phage was felt to provide an adequate example for a demonstration of the method of the invention. Second, λ phage has been well studied and is readily available.

EXAMPLE 1

Sample bacteriophage λ-DNA was obtained from Bethesda Research Laboratories in Gaithersburg, Md., Catalogue Number 5250. The target sequence chosen corresponds to the sequence of nucleotides starting at base 145 and ending at base 224. (See "Nucleotide Sequence of cro, c II, and part of the O gene in Phage λ-DNA," E. Schwarz, et al., *Nature*, 272, Mar. 30, 1978.)

The diagnostic portion chosen was a 15-mer corresponding to the sequence of nucleotides starting at base 145 and ending at 159 in the λ-DNA. The diagnostic probe, a 15-mer complementary to the diagnostic sequence, was synthesized on an Applied Biosystems 380A DNA synthesizer, and had the sequence 5'-ATCAGCGTTTATAGT-3'. The contiguous portion chosen was a sequence 65 bases long contiguous with the diagnostic sequence, i.e., beginning at base 160 and ending at base 224. The contiguous probe, a 65-mer complementary to the contiguous portion, was also synthesized on an Applied Biosystems 380A DNA synthesizer, and had the sequence 5'-GTTATTTATGCTGTTGTTTTTTTGTTACT CGGGAAGGGCTTTACCTCTTCCGCATAAACGCTT CC-3'. The 15-mer was phosphorylated with $^{32}$P using $T_4$ polynucleotide kinase, thereby also radioactively labeling the 15-mer. (See Appendix B for the specifics of this kinasing process.)

The sample DNA was denatured and immobilized (as described in Appendix A, except that Schleicher & Schuell BA85 nitrocellulose filter was used cut in 9 mm diameter circles), and non-specific binding sites were blocked, as described earlier under Sample Preparation. About 0.3 pmol phage λ-DNA was fixed onto the nitrocellulose filter paper during this sample preparation process.

Step 1.

The 65-mer was hybridized to the λ-DNA by incubating the DNA-paper with 150 μl 2×SSC containing 4 pmol 65-mer for 3 hours at 57° C., and the 65-mer solution was removed. (2×SSC is 0.3M NaCl, 0.03M Na citrate pH 7.0.)

Step 2.

The 15-mer was hybridized to the λ-DNA by incubating the DNA paper with 150 μl 2×SSC containing 4 pmol of the labeled 15-mer for 16 hours at 36° C.

Step 2a.

A substantial portion of the 15-mer not perfectly bound (i.e., not bound at all 15 sites) in Step 2 was removed by washing the DNA-paper in 320 ml 2×SSC for 10 minutes at 23° C. and then washing the filter again in 2 μl of the buffer 66 mM Tris HCl at pH 7.5, 6.6 mM $MgCl_2$, and 10M dithiothreitol.

Step 3.

The two probes were ligated by incubating the DNA-paper in 150 μl of the buffer used in Step 2a, plus 0.4 mM ATP and 2 μl $T_4$ DNA ligase for 2 hours at 23° C.

Step 4.

The stringency was increased to remove nearly all of the labeled probe that was not ligated in Step 4. This was accomplished by washing the DNA-paper, by passing 200 μl/min of 2×SSC through the filter at 28° C. for 1 hour. Although it was designed for another purpose, an Applied Biosystems 470A Protein Sequencer was used for this operation, since it has a cartridge assembly which can hold a filter and can be programmed to deliver liquids through the filter at a programmable temperature.

To detect the ligated probes (the target probe), the stringency was further increased by increasing the temperature 5° C./hr and passing 0.1×SSC with 0.5% sodium dodecyl sulfate through the filter. Fractions of 200 μl each were collected every 45 minutes. The radioactivity of each fraction was then determined using a liquid scintillation counter and the number of cumulative counts at the end of each interval was plotted versus temperature.

Figure 3:
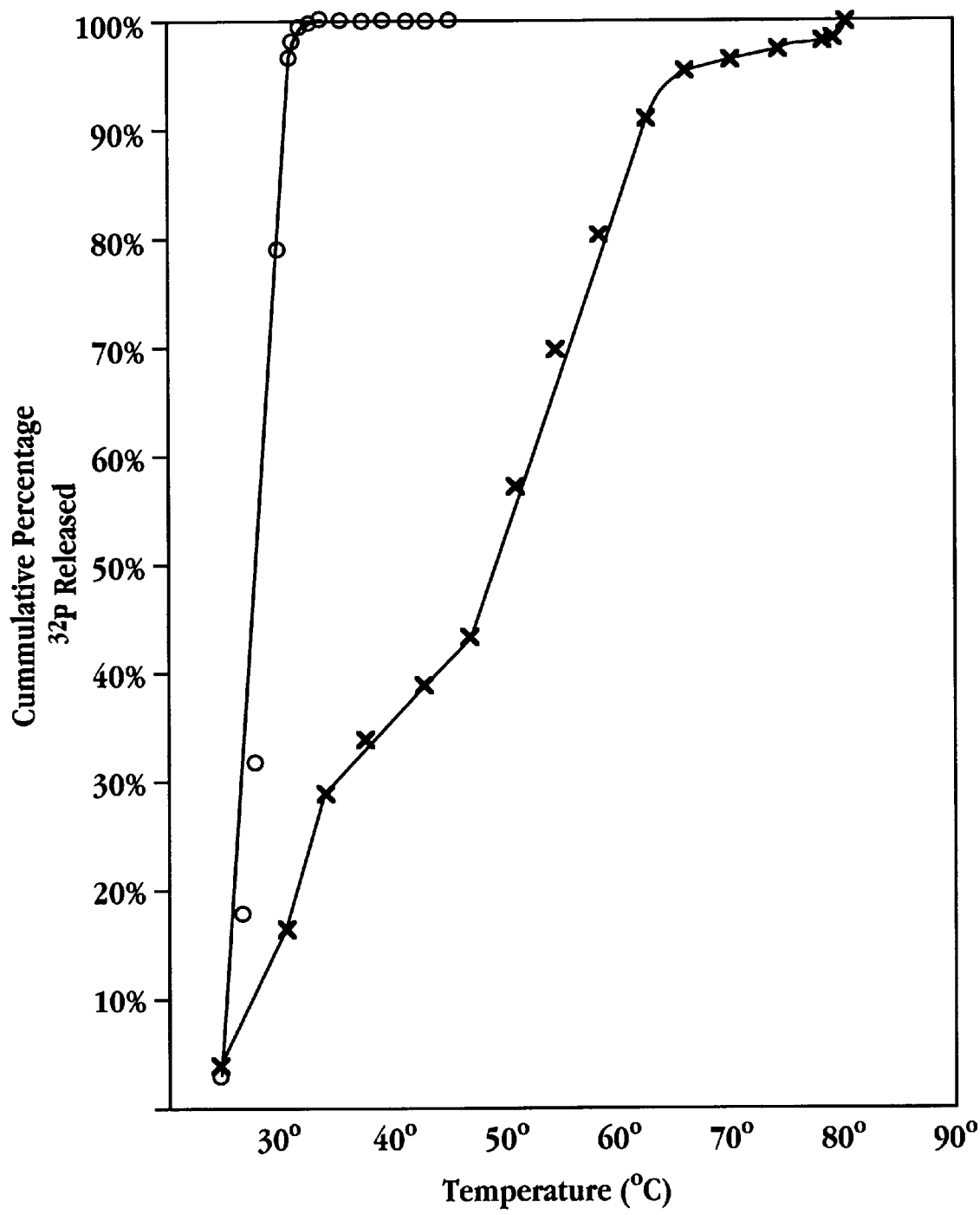
FIG. 3 shows the results of a melting curve analysis of a 15-mer hybridized to a λ-phage DNA sample and of an 80-mer made up of the same 15-mer ligated to a 65-mer which was hybridized adjacent to the 15-mer on the same substrate.

FIG. 3 shows the results of this procedure. For comparison purposes, this was also done for the case where no ligase was used. As can be seen, the use of the ligase dramatically changed the melting curve relative to the unligated case. Essentially all of the unligated labeled probe was dissociated by the time the temperature reached 35° C. Whereas, in the ligated case, a substantial portion of the labeled 80-mer remained at 35° C. Hence, by restricting the measurement of radioactivity to material removed from the filter above 35° C., essentially only ligated probe will be counted. The fact that the 80-mer was all that was being counted above 35° C. was further verified by SDS polyacrylamide gel electrophoresis.

In the context of the general method and the specific example described above, certain aspects of the protocol should be noted. As a general rule, it is preferred that the diagnostic probe be relatively short in absolute terms in order to be able to detect single base pair mismatches. This selectivity is accomplished by removing the diagnostic probe which is not perfectly bound by washing at stringency, as in Step 1a or Step 2a following the hybridization procedure, depending on the step at which the diagnostic probe is hybridized.

In practice, it is of course not practical to remove 100% of the labeled probe not perfectly bound, since to do so would also remove a substantial percentage of the perfectly bound probe. However, for a 15-mer, it is practical to remove over 70% of the labeled probe not perfectly bound, and preferably over 90%. In the usual application of the method, it is only necessary to remove enough imperfectly bound labeled probe to permit differences between homozygous and heterozygous cells to be unequivocally determined. Any imperfectly bound labeled probe which remains hybridized to the target sequence can become ligated and will contribute background noise in the measurements to be made later. Hence, the amount of imperfectly bound labeled probe it is necessary to remove will depend on how much background can be tolerated in arriving at a statistically valid determination.

In the example presented, which is the preferred mode, the labeled probe and the diagnostic probe are the same. A 15-mer was chosen as the diagnostic probe because it was short enough in length to permit any imperfectly bound probe to be readily separated by changes in stringency. The unlabeled probe, i.e., the contiguous probe, was chosen to be sufficiently long to provide a high specificity and a meaningful change in melting point when ligated, and was sufficiently short to hybridize rapidly and could be readily synthesized.

In the unusual situation where the contiguous probe is labeled instead of the diagnostic probe, the diagnostic probe must still be small enough to be able to have specific binding to different alleles which can be differentiated by changes in stringency. Also, the labeled contiguous probe must be small enough to provide a significant change in melting point when ligated to the diagnostic probe so that unligated labeled contiguous probe can be removed before the ligated probe is eluted, while at the same time it must be long enough that the contiguous probe and diagnostic probe together bind to a unique sequence.

From the above discussion, it should also be apparent that the use of a 15-mer and a 65-mer in the example is merely illustrative, and that many other combinations of probe lengths are available. For example, in some situations it may be desirable to use a very short diagnostic probe, perhaps in the range of four to five base pairs in length to further facilitate differentiation of matched and mismatched diagnostic probes by changes in stringency. As a practical matter, however, it should be noted that for the method to offer advantages over the prior art techniques, the length of the ligated probes together must not only be long enough to define a unique sequence to be detected, but also long enough that non-specific binding to sites not in the sequence of interest will not cause excessive background as occurs in the prior art. With regard to the former, clearly the longer the sequence, the more likely it is to be unique. The current art appears to have settled on a definition of a unique sequence as being about 19 nucleotides in length for mammalian genomic DNA, which corresponds roughly to the maximum length which can be reasonably distinguished with presently available techniques using differences in stringency. Given these considerations, at the present time the preferred length for the diagnostic probe ranges from about four base pairs to about nineteen base pairs. With regard to non-specific binding, a minimum combined ligated (target) probe length is unresolved and may vary from gene to gene. From present experiments, however, it appears that an 80-mer is more than adequate, and that an adequate range of lengths would be from about 20 base pairs to about 80 base pairs. In situations, however, where the diagnostic probe is the labeled probe, there appears to be no detriment other than hybridization time and manufacturing considerations to the use of much longer contiguous probes, for example, up to many thousand base pairs as might be the case if the contiguous probe is a cloned sequence. Hence, in the preferred mode, the lengths for the combined (target) probes ranges upward from about 19 nucleotides.

Some of this size dependency created by using differences in stringency to remove unligated probe can be eliminated by using an alternative technique to recover the ligated probes. For example, it may be useful to provide one of the probes (the unlabeled probe) with a hook so that the ligated (target) probe can be recovered after Step 4 by catching the hook rather than by increasing the stringency. One such approach which appears particularly promising is to attach biotin to the contiguous probe before hybridizing it to the nucleic acid. Steps 1 through 4 in the above method are followed as before and the ligated probe is recovered using streptavidin to bind the biotin molecules contained in the ligated probe. With this approach, relative size is no longer an issue, except that the diagnostic probe must as always be short enough to distinguish single base pair mismatches, and the contiguous probe and diagnostic probe together must be long enough to bind to a unique site. The specifics of this biotin-avidin recovery process which illustrates the general approach are outlined below in Example 2.

EXAMPLE 2

A sample DNA is prepared and the diagnostic and contiguous probes are obtained as previously described. A biotin moiety is then attached to the 3'OH of the contiguous probe, e.g., by using an Enzo Bio-Probe™ Terminal Labeling Kit. Another approach for attaching biotin which is a variation on the Enzo Bio-Probe™ process entails mixing about 1 μg of DNA probe with 0.2M potassium cacodylate buffer pH7.0, 1 mM $CoCl_{21}$ 0.1 mM biotinylated dUTP, and incubating for one hour at 37° C. or until an average of one biotin per DNA probe has been incorporated. The contiguous probe is then phosphorylated (not labeled) and the diagnostic probe is labeled either at the 5' OH or internally. Steps 1 through 4 are then carried out as before. The recovery process for the ligated probes is effected by increasing the stringency, e.g., by raising the temperature, and then placing the eluted material in close contact with bound avidin, e.g., by passing the eluted material through a porous substrate covalently coated with streptavidin, or incubating the eluted material in a vessel coated with streptavidin. (Streptavidin is an intracellular product of Streptomyces Avidinii. See L. Chaiet and F. J. Wolf, *Arch. Biochem. and Biophys.* 106: 1–5.) Typical substrates include nitrocellulose filter paper or small beads (generally 3 to 30 microns in diameter). The labeled ligated probe will be concentrated on the porous substrate if and only if it contains the biotin hook (i.e., if a hooked probe and a labeled probe are ligated). This process is particularly useful in concentrating label, for instance, as is often desired with fluorescent labeling schemes. Note also that careful control of temperature is not required to selectively dissociate unligated probe.

Application of the above methods of the invention to the detection of genetic diseases is relatively straightforward. For example, in the detection of sickle-cell disease, it is necessary to distinguish DNA of homozygous individuals with the normal β-globin gene, ($\beta^A\beta^A$), from that of heterozygous individuals with sickle-cell trait having $\beta^S$ allele, ($\beta^A\beta^S$), from that of individuals having sickle-cell disease, ($\beta^S\beta^S$). In one approach, two diagnostic probes are synthesized, one specific to the normal β-globin ($\beta^A$) and one specific to the sickle-cell allele ($\beta^S$) Also, the contiguous probe which will be adjacent to these two first probes when hybridized to the test DNA is synthesized and Steps 1 through 4 above are carried out separately for each diagnostic probe. The DNA from individuals homozygous for the normal β-globin gene will then show a high count for the probe specific to the normal gene $\beta^A$, and a low count for the probe specific to the $\beta^S$ allele. Similarly, the DNA from individuals homozygous for the sickle-cell β-globin gene will show a high count for the probe specific to the $\beta^S$ allele and a low count for the probe specific to the normal gene $\beta^A$. DNA from heterozygous individuals ($\beta^A\beta^S$) will show substantially equal counts from both of the specific diagnostic probes, that count in magnitude being intermediate between the high and low counts discussed above for homozygous individuals.

In another approach, a single diagnostic probe specific to the $\beta^S$ allele can be used in Steps 1 through 4 above, provided adequate controls are used to insure reproducible results. Here total counts are calibrated to distinguish directly normal genotypes without sickle-cell trait or disease (i.e., $\beta^A\beta^A$) from $\beta^A\beta^S$, and $\beta^S\beta^S$ genotypes. In this approach, although it is preferable to use a probe specific to the $\beta^S$ allele in order to have a positive indication of sickle-cell trait or disease, it should be understood that it is also possible to use a probe specific to the normal genotype to indicate sickle-cell allele, provided that there are no other genetic diseases which might yield a low or intermediate count when hybridized with the normal probe specific to the sequence in the test DNA having a location where the sickle-cell base pair mutation occurs.

While preferred embodiments of the present invention have been described, it will be apparent to those skilled in the art that many changes and modifications may be made without departing from the invention in its broader aspects. For example, it is clear that the contiguous probe may be either direction along the nucleic acid, or that the contiguous probe may be either longer or shorter than the diagnostic probe, depending on the particular target sequence it is desired to identify. Also, the above techniques are useful in determining if a specific sequence is located next to another specific sequence in a DNA chain, or similarly a series of probes each adjacent the next could be used to demonstrate the proximity of specific sequences or to increase the size of the ligated probes. Therefore, the appended claims are intended to cover all such modifications, changes, and applications that fall within the true spirit and scope of the invention.

We claim:

1. A kit for determining the presence or absence of a target polynucleotide sequence in a nucleic acid sample, said kit comprising:

a first probe which is complementary to a first region of a target sequence, a second probe which is complementary to a second region of the target sequence, where said first and second target regions are contiguous with one another, and said first and second probes are capable of being ligated to each other when hybridized to such contiguous first and second target regions, a third probe which is complemnentary to a third target region of the target sequence which is continuous with the first target region, such that said second and third target regions correspond to alternative allelic sequences or to a normal and mutated sequence, and ligation means capable of ligating first and second probes, or first and third probes, that have hybridized specifically to contiguous target regions to which the first and second probes, or first and third probes, are complementary, respectively.

2. The kit of claim 1, wherein said ligation means is a ligase enzyme.

3. The kit of claim 1, wherein at least one of said probes contains a label that allows specific detection of said labeled probe in the presence of unlabeled nucleic acids.

4. The kit of claim 3, wherein said label is radioactive.

5. The kit of claim 3, wherein said label is a fluorescent label.

6. The kit of claim 3, wherein said label is an enzyme.

7. The kit of claim 1, wherein at least one of said probes includes non-polynucleotide hook moiety for capture of the probe on a support.

8. The kit of claim 7, wherein said hook moiety is a biotin moiety.

9. The kit of claim 7, wherein said hook moiety is an antigen, and the kit further includes an antibody which is immunospecific for the antigen.

10. The kit of claim 7, wherein said hook moiety is a ligand, and the kit further includes a receptor which can bind specifically to the ligand.

11. The kit of claim 1, which further includes instructions for performing ligation of the first and second probes, or first and third probes, when bound to contiguous target regions, to detect whether a target polynucleotide sequence complementary to the first and second probes, or first and third probes, is present in the sample.

12. The kit of claim 11, wherein said ligation means is a ligase enzyme.

13. The kit of claim 11, wherein at least one of said probes contains a label that allows specific detection of said labeled probe in the presence of unlabeled nucleic acids.

14. The kit of claim 13, wherein said label is radioactive.

15. The kit of claim 13, wherein said label is a fluorescent label.

16. The kit of claim 13, wherein said label is an enzyme.

17. The kit of claim 11, wherein at least one of said probes includes a non-polynucleotide hook moiety for capture of the probe on a support.

18. The kit of claim 17, wherein said hook moiety is a biotin moiety.

19. The kit of claim 17, wherein said hook moiety is an antigen, and the kit further includes an antibody which is immunospecific for the antigen.

20. The kit of claim 17, wherein said hook moiety is a ligand, and the kit further includes a receptor which can bind specifically to the ligand.

* * * * *